(12) United States Patent
Noweck et al.

(10) Patent No.: US 6,517,795 B1
(45) Date of Patent: Feb. 11, 2003

(54) PROCESS FOR PRODUCING HYDROTALCITES AND THE METAL OXIDES THEREOF

(75) Inventors: Klaus Noweck, Brunsbuttel; Klaus Diblitz, Schenefeld; Jan Sohiefler, Hamburg; Andrea Brasch, Meldorf, all of (DE)

(73) Assignee: Sasol Germany GmbH, Hamburg (DE)

( * ) Notice: Subject to any disclaimer, the term of this patent is extended or adjusted under 35 U.S.C. 154(b) by 1036 days.

(21) Appl. No.: 08/875,528

(22) Filed: Jul. 31, 1997

(30) Foreign Application Priority Data

Feb. 3, 1995 (DE) .......................... 195 03 522

(51) Int. Cl.$^7$ .......................... C01F 1/00; C01F 17/00; C01G 3/00; C01G 9/00
(52) U.S. Cl. .......................... 423/263; 423/593; 423/594; 423/595; 423/599; 423/600; 534/15; 534/16; 556/1; 556/13; 556/15; 556/16; 556/19; 556/43; 556/44; 556/46; 556/49; 556/58; 556/61; 556/62; 556/87; 556/90; 556/112; 556/114; 556/121; 556/131; 556/140; 556/143; 556/147
(58) Field of Search ................. 423/593, 594, 423/595, 599, 600, 263; 534/15, 16; 556/1, 13, 15, 16, 19, 43, 44, 46, 49, 58, 61, 62, 87, 90, 112, 114, 121, 131, 140, 143, 147

(56) References Cited

U.S. PATENT DOCUMENTS

| | | | |
|---|---|---|---|
| 3,650,704 A | | 3/1972 | Kumura et al. ............... 23/315 |
| 3,879,523 A | * | 4/1975 | Miyata et al. ............... 423/593 |
| 3,879,525 A | * | 4/1975 | Miyata et al. ............... 423/593 |
| 4,351,814 A | * | 9/1982 | Miyata et al. ............... 423/306 |
| 4,539,306 A | | 9/1985 | Chang ........................ 502/154 |
| 4,543,341 A | * | 9/1985 | Barringer et al. ........... 423/593 |
| 4,629,626 A | * | 12/1986 | Miyata et al. ............... 423/594 |
| 4,636,248 A | * | 1/1987 | Ogata et al. ................ 423/593 |
| 4,774,212 A | | 9/1988 | Drezdon ...................... 502/62 |
| 4,843,168 A | | 6/1989 | Drezdzon et al. ........... 558/357 |
| 4,968,498 A | * | 11/1990 | Wautier et al. .............. 423/593 |
| 5,075,089 A | | 12/1991 | Misra et al. ................. 423/331 |
| 5,084,209 A | | 1/1992 | Burba, III et al. ........ 252/315.5 |

FOREIGN PATENT DOCUMENTS

| | | |
|---|---|---|
| EP | 0065863 | 12/1982 |
| EP | 0103034 | 3/1984 |
| EP | 0131685 | 1/1985 |
| EP | 0207811 | 1/1987 |
| EP | 0484829 | 5/1992 |
| EP | 0536879 | 4/1993 |
| WO | 9321961 | 11/1993 |
| WO | 9322237 | 11/1993 |
| WO | 9324411 | 12/1993 |

OTHER PUBLICATIONS

S. Miyata, et al., "Synthesis of Hydrotalcite–Like Compounds and Their Physico–Chemical Properties," *Clays and Clay Minerals*, vol. 25, 1977, pp. 14–18, No Month.
W. T. Reichle, "Catalytic Reactions by Thermally Activated, Synthetic, Anionic Clay Minerals," *Journal of Catalysis*, vol. 94, 1985, pp. 547–557, No Month.
J. G. Nunan, et al., "Methanol Synthesis Catalysts Based on Cs/Cu/ZnO/$M_2O_3$(M = Al, Cr, Ga): Genesis from Coprecipitated Hydrotalcite–like Precursors, Solid–State Chemistry, Morphology, and Stability," *Inorganic Chemistry*, vol. 28, 1989, pp. 3868–3874, No Month.
M. Meyn, et al., "Anion–Exchange Reactions of Layered Double Hydroxides," *Inorganic Chemistry*, vol. 29, 1990, pp. 5201–5207, 1990, No Month.
M. Drezdzon, "Pillared Hydrotalcites: Synthesis, Characterization, and Catalytic Activity," *ACS–Symposium Series—Novel Materials in Heterogenous Catalysis*, vol. 437, 1990, pp. 140–148, No Month.
F. Cavani, et al., "Hydrotalcite–Type Anionic Clays: Preparation, Properties and Applications," *Catalysis Today*, vol. 11, 1991, pp. 173–291, No Month.
A. L. McKenzie, et al., "Investigation of the Surface Structure and Basic Properties of Calcined Hydrotalcites," *Journal of Catalysis*, vol. 138, 1992, pp. 547–561, No Month.

* cited by examiner

*Primary Examiner*—Steven Bos
(74) *Attorney, Agent, or Firm*—Madan, Mossman & Sriram, P.C.

(57) ABSTRACT

A process for producing high-purity hydrotalcites by reacting alcohols or alcohol mixtures with at least one or more divalent metal(s) and at least one or more trivalent metal(s) and hydrolyzing the resultant alcoholate mixture with water. The corresponding metal oxides can be produced by calcination.

18 Claims, 2 Drawing Sheets

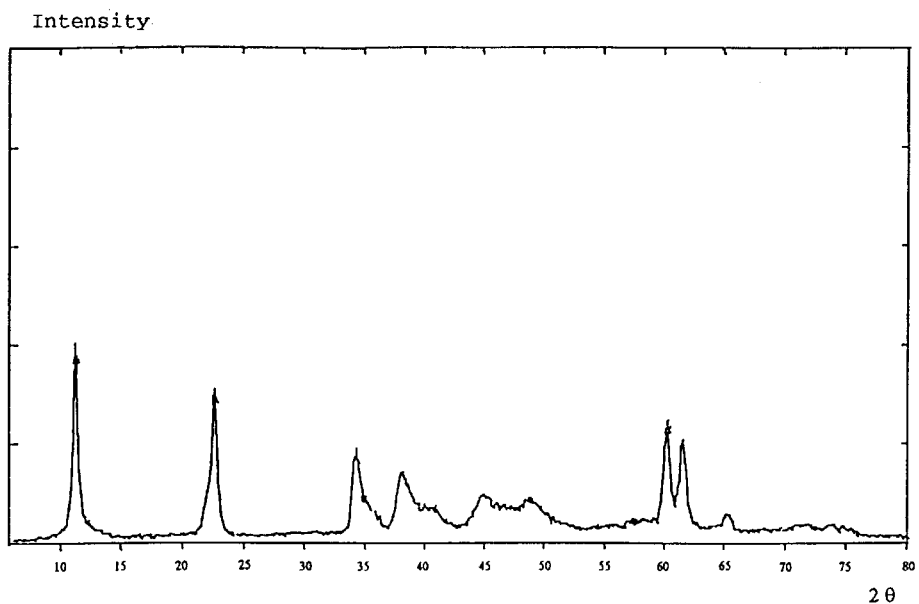
Fig. 1  X-Ray Diffraction Pattern of $Mg_6Al_2(OH)_{18} \cdot 4\ H_2O$
(Compound 6 in Table I)
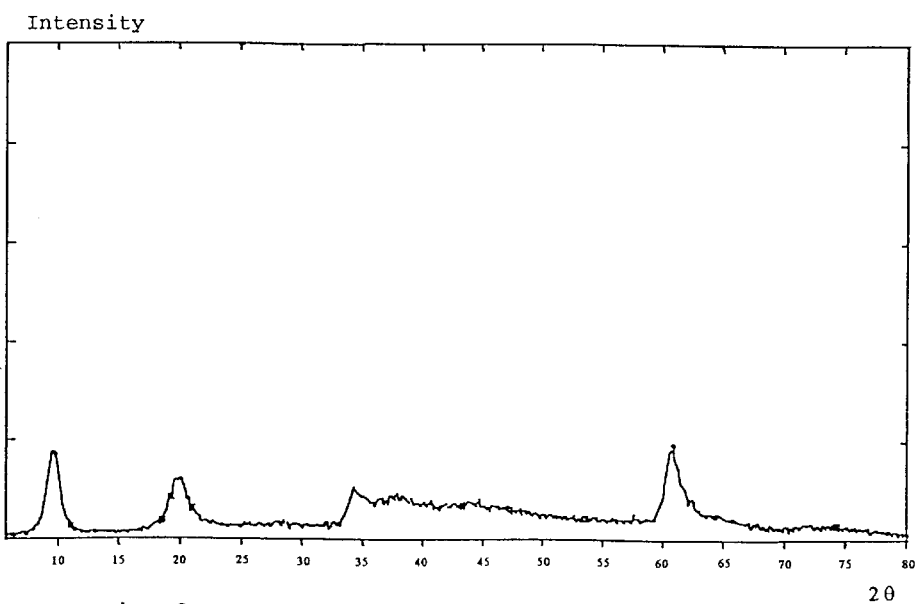
Fig. 2  X-Ray Diffraction Pattern of
$Mg_6Al_2(OH)_{16}(NO_3)_2 \cdot 4\ H_2O$
(Compound 9 in Table I)

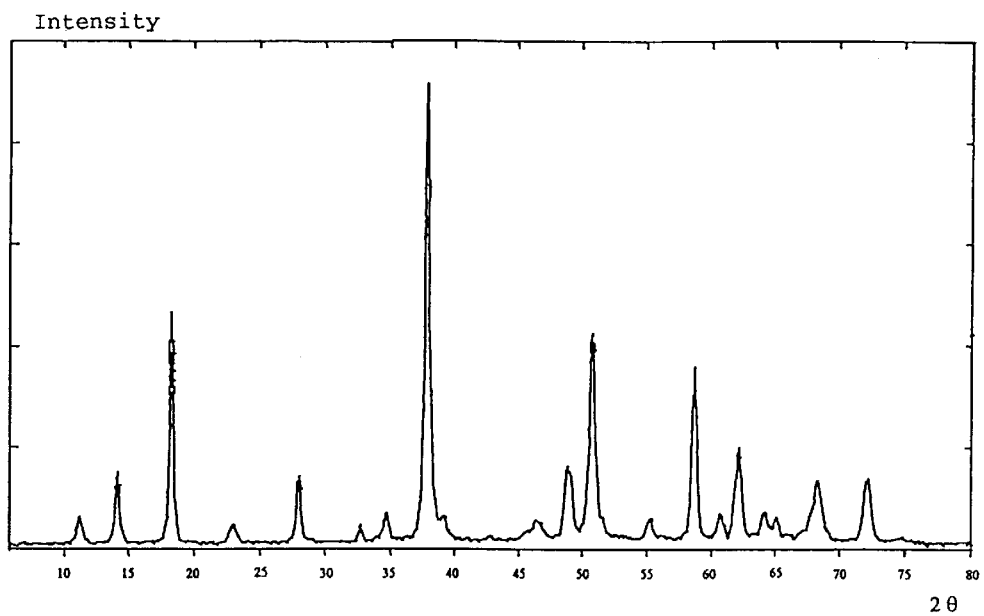
Fig. 3  X-Ray Diffraction Pattern of a Mixture of Aluminium Hydroxide and Magnesium Hydroxide as a Reference Product
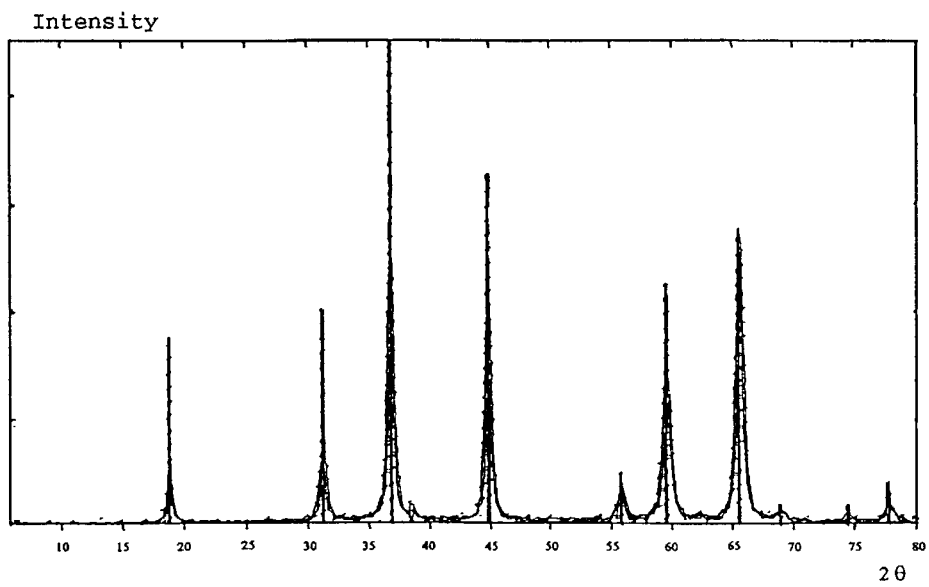
Fig. 4  X-Ray Diffraction Pattern of $MgAl_2O_4$, a Spinel Produced According to this Invention

PROCESS FOR PRODUCING HYDROTALCITES AND THE METAL OXIDES THEREOF

The present invention relates to the production of hydrotalcites. Hydrotalcites are metal hydroxides having a layer lattice and belonging to the group of anionic clay minerals. Furthermore, the present invention relates to the metal oxides obtained by calcination of the metal hydroxides produced according to this invention.

Metal hydroxides are important precursors for the production of metal oxides used for instance as raw materials for refractories, ceramics, and supports for heterogeneous catalysts. In nature, metal hydroxides predominantly occur in the form of mixed metal hydroxides. There are numerous clay minerals that can be characterised by their layer lattice. The great majority of clay minerals are cationic ones. In said metal hydroxides, cations, e.g. $Na^+$, $Ca^{2+}$, etc., are located between the negatively charged layers. In anionic clay minerals which are far less common, anions are located between the positively charged layers of the metal hydroxide. A large number of said anionic clay minerals are hydroxides of metals of the main group, namely magnesium and aluminium, and hydroxides of transition metals, such as nickel, chromium, zinc, etc. The structure of said clay minerals can be derived from the brucite structure of magnesium hydroxide $Mg(OH)_2$. In this structure, some of the divalent $Mg(OH)_6^{4-}$ octahedra are replaced by $Al(OH)_6^{3-}$ octahedra. Examples of said minerals are meixnerite having the idealised unit cell formula $Mg_6Al_2(OH)_{18} \cdot 4\ H_2O$ and hydrotalcite $(Mg_6Al_2(OH)_{16}CO_3 \cdot 4\ H_2O)$. According to the prior art, the magnesium : aluminium atomic ratios can be varied between 1.7 and 4.0. The metal hydroxide octahedra share adjacent edges to form layers. In addition to water, interstitial anions required for balancing the charge are located between the layers. The anion nature can be simple, e.g. $OH^{31}$, $CO_3^{2-}$, $Cl^{31}$ or $SO_4^{2-}$, or complex, as for instance in large, organic or inorganic anions. Up to now, such anions have been incorporated into the layers by substitution of simple anions or by acid treatment in the presence of the desired anions.

Numerous processes for producing stratiform, anionic clay minerals are known in the art. All of these processes employ metal salts as starting materials which are dissolved and then mixed with each other at defined pH-values. See e.g. U.S. Pat. Specification No. 4,539,306 describing the production of hydrotalcites for pharmaceutical use, and Reichle, W. T., *Journal of Catalysis*, Vol. 94 (1985), p. 547–557, and Nunan, J. G., et al., *Inorganic Chemistry*, Vol. 28 (1989), p. 3868–3874. Misra et al. have disclosed the production of hydrotalcites having interstitial anions which increase the interlayer spacing by exchanging the anions at elevated temperatures (cf. U.S. Pat. Specification No. 5,075,089). Examples of the incorporation of large, organic anions by anion exchange are given by Lagaly, G., et al. in *Inorganic Chemistry*, Vol. 29 (1990), p. 5201–5207. Miyata et al. have described the production of magnesium/aluminium hydrotalcites by mixing solutions of the salts $MgCl_2$ and $Al_2(SO_4)_3$ and a NaOH solution (cf. *Clay and Minerals*, Vol. 25 (1977), p. 14–18). EP-A1-0 536 879 proposes the production of stratiform, anionic clay minerals by using inorganic anions which increase the interlayer spacing, such as $B(OH)_4^-$, $V_4O_{12}^{4-}$, $V_2O_7^{4-}$, or $HV_2O_7^{3-}$. In said publication, too, solutions of metal salts are mixed at defined pH-values with solutions of the salts that are to be incorporated. Examples of the uses of stratiform, anionic clay minerals as catalysts are given in U.S. Pat. Specification No. 4,774,212, U.S. Pat. Specification No. 4,843,168, EP-A1-0 536 879, and by Drezdon, M. in *ACS Symp. Ser.*, (*Novel Mater. Heterog. Catal.*), Vol. 437 (1990), p. 140–148.

WO-A-93 21 961 describes a process for manufacturing of stratiform, mixed metal hydroxides through controlled hydrolysis of metal oxides in a water free organic solvent with stoichiometric amounts of water. The thereby obtained metal hydroxides are gel-compositions for use as a dye carrier in dye laser applications. According to the bottom of page 4 this metal hydroxides have the following composition

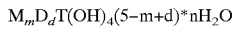

$$M_m D_d T(OH)_4 (5-m+d) * nH_2O$$

wherein M, D, T are monovalent, divalent or trivalent metals, m=0 to 1, d=0 to 1 whereby m+d≠0. The hereby obtained metal hydroxides are no chemical compounds, but gel-like compositions which are unsuitable as precursors for preparing metal oxides of defined structure according to the scope of the present invention.

The wide use of stratiform, anionic clay minerals has been impeded up to now by the fact that for the production starting from metal salt solutions only a time-consuming, discontinuous synthesis route is known.

Furthermore, catalyst purity is a generally accepted, essential criterion. Contaminations caused by alkali—and alkaline earth metals are particularly undesirable. However, when using metal salts, said contaminants cannot be avoided, or they can only be avoided by great efforts involving high costs. Moreover, there is no process known for producing clay minerals of the hydrotalcite type with only $OH_{31}$ -ions located in the layers without additional, subsequent ion exchange.

The most important criterion for the catalytic properties of said clay minerals is their basicity. According to the prior art, the basicity is substantially determined by the Mg:Al ratio. See McKenzie, A. L., Fishel, C. T., and Davis, R. J. in *J. Catal.*, Vol. 138 (1992), p. 547. Therefore, in order to adjust the catalytic characteristics of a catalyst, it is desirable to provide the widest possible variation of the Mg:Al ratio. Furthermore, it has been unknown up to now to produce stratiform, anionic clay minerals with a Mg:Al ratio of less than 1.7.

It is the object of the present invention to provide a process for producing stratiform, anionic clay minerals having the following advantages:

- time-saving synthesis which can be carried out both continuously and discontinuously
- use of inexpensive and readily available starting materials
- high purities and low alkali concentrations of the stratiform, anionic clay minerals produced by said process
- optionally, the possibility of producing stratiform, anionic clay minerals comprising only hydroxide ions as interstitial anions
- production of stratiform, anionic clay minerals having sufficiently large pore volumes and surface areas required for catalysis
- production of stratiform, anionic clay minerals having a Mg:Al ratio of less than 1.7.

According to the present invention there is provided a process for producing high-purity hydrotalcites which are stratiform, anionic, mixed metal hydroxides of the general formula

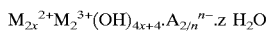

$$M_{2x}^{2+} M_2^{3+}(OH)_{4x+4} \cdot A_{2/n}^{n-} \cdot z\ H_2O$$

wherein x ranges from 0.5 to 10 in intervals of 0.5, A is an interstitial anion, n is the charge of said interstitial anion which is up to 8, normally up to 4, and z is an integer of 1 to 6, particularly 2 to 4, wherein (A) metal alcoholate mixtures comprising at least one or more divalent metal(s), at least one or more trivalent metal(s), and mono-, di-, or trihydric $C_1$ to $C_{40}$ alcoholates are used, said means di- and trihydric metal alcoholates being substantially used in a molar ratio corresponding to the stoichiometry of any desired compound according to the empirical formula referred to hereinabove, and (B) the resultant alcoholate mixture is hydrolysed with water, the water for hydrolysis being used in stoichiometric excess, referring to the reactive valences of the metals used.

The corresponding mixed metal oxide can be produced therefrom by calcination.

The metal alcoholates can be produced by reacting metals having the oxidation numbers +II or +III with mono-, di- or trihydric $C_1$ to $C_{40}$ alcohols. The production of the metal alcoholates can be accomplished by (A) placing the metals jointly into the reaction vessel and then adding the alcohol, or (B) producing the metal alcoholates separately, the alcoholates optionally having different alcoholate residues, or (C) consecutively, i.e. by placing one metal into the reaction vessel, adding the alcohol, followed by addition of the second metal, and, optionally, of further amounts of alcohol.

Divalent metals suitable for the production of said alcoholates are Mg, Zn, Cu, Ni, Co, Mn, Ca and/or Fe. Suitable trivalent metals are Al, Fe, Co, Mn, La, Ce and/or Cr.

Prior to or during hydrolysis, any water-soluble, di- or trivalent metals can be added as metal salts, the metal salts being used in smaller stoichiometric quantities than the metal alcoholates.

The metal alcoholates are produced such that the molar ratio of divalent : trivalent metal alcoholates is from 1:2 to 10:1. They are subsequently hydrolysed. Prior to hydrolysis, the alcoholate (alcoholate mixture) may be filtered to separate any insoluble component.

Suitable alcohols are mono-, di-, and trihydric alcohols having chain lengths of $C_1$ to C40. They can be branched, unbranched, or cyclic, but branched and unbranched alcohols with chain lengths of $C_4$ to $C_{20}$ are preferred, and chain lengths of $C_6$ to $C_{14}$ are particularly preferred.

For the production of stratiform, anionic clay minerals according to this invention, the metal alkoxides may be produced from the same alcohols or mixtures of alcohols.

For the production of high-purity clay minerals, the water used for hydrolysis is purified by ion exchange or repeated distillation. Hydroxide anions and/or any other water-soluble anions can be added to the water for hydrolysis. As organic anions, alcoholate anions are particularly preferred, but alkyl ether sulfates, aryl ether sulfates and/or glycol ether sulfates are also suitable; and/or inorganic anions can be used, particularly carbonate, hydrogen carbonate, nitrate, chloride, sulfate, $B(OH)_{4-}$; and/or polyoxometal anions, such as $Mo_7O_{24}^{6-}$ or $V_{10}O_{28}^{6-}$, are also suitable. $NH_4^+$ is the preferred gegenion. The anions are incorporated as interstitial anions into the lattices of the stratiform clay minerals formed during hydrolysis, or they are incorporated subsequently by anion exchange as interstitial anions into the stratiform, anionic clay minerals.

The pH-value of the water for hydrolysis may be in the range of 0 to 14, preferably 1 to 13. The temperature of the water for hydrolysis may be from 5 to 98° C., preferably 20 to 95° C., most preferably 30 to 90° C.

The hydrotalcites produced according to this invention have interlayer spacings (d-values) of greater than 7 Å, measured on the d(003) reflex. The compositions and physical data of Mg(Zn)/Al clay minerals produced according to the invention are listed in Table I.

TABLE I

| C.* | Al/M$^{2+}$ | Formula | Surf.*$^a$ [m$^2$g] | PV*$^a$ [ml/g] | PR*$^a$ [Å] | CS*$^b$ [Å] | dV*$^b$ [Å] |
|---|---|---|---|---|---|---|---|
| 1 | 2:1 | MgAl$_2$(OH)$_8$.4 H$_2$O | 244 | 0.26 | 23 | | 7.72 |
| 2 | 1:1 | Mg$_2$Al$_2$(OH)$_{10}$.4 H$_2$O | 217 | 0.43 | 26 | 210 | 7.78 |
| 3 | 1:2.5 | Mg$_5$Al$_4$(OH)$_{22}$.4 H$_2$O | 230 | 0.13 | 29 | | 8.22 |
| 4 | 1:1.5 | Mg$_3$Al$_2$(OH)$_{12}$.4 H$_2$O | 276 | 0.78 | 51 | | 7.82 |
| 5 | 1:2 | Mg$_4$Al$_2$(OH)$_{14}$.4 H$_2$O | 283 | 0.69 | 43 | 230 | 7.79 |
| 6 | 1:3 | Mg$_6$Al$_2$(OH)$_{18}$.4 H$_2$O | 190 | 0.39 | 161 | | 7.73 |
| 7 | 1:5 | Mg$_{10}$Al$_2$(OH)$_{26}$.4 H$_2$O | 197 | 0.29 | 25 | | |
| 8 | 1:10 | Mg$_{20}$Al$_2$(OH)$_{46}$.4 H$_2$O | 181 | 0.35 | 32 | 420 | |
| 9 | 1:3 | Mg$_6$Al$_2$(OH)$_{16}$(NO$_3$)$_2$.4 H$_2$O | 180 | 0.32 | 29 | | 8.73 |
| 10 | 1:3 | Mg$_6$Al$_2$(OH)$_{16}$(HCO$_3$)$_2$.4 H$_2$O | 190 | 0.76 | 174 | 400 | 7.79 |
| 11 | 1:3 | Mg$_6$Al$_2$(OH)$_{16}$CO$_3$.4 H$_2$O | 182 | 0.77 | 217 | | 7.77 |
| 12 | 1:3 | Mg$_{18}$Al$_6$(OH)$_{48}$(Mo$_7$O$_{24}$).4 H$_2$O | 26 | 0.06 | 22 | | 9.26 |
| 13 | 1:3 | Mg$_6$Al$_2$(OH)$_{16}$(C$_6$H$_6$O$_7$).4 H$_2$O | 330 | 0.29 | 19 | | 11.23 |
| 14 | 1:3 | Mg$_6$Al$_2$(OH)$_{16}$(C$_3$H$_5$O$_2$)$_2$.4 H$_2$O | 236 | 0.57 | 37 | 200 | 13.22 |
| 15 | 1:1.5 | Mg$_3$Al$_2$(OH)$_{10}$(NO$_3$)$_2$.4 H$_2$O | 145 | 0.24 | 26 | | 8.98 |
| 16 | 1:1.5 | Mg$_3$Al$_2$(OH)$_{10}$(HCO$_3$)$_2$.4 H$_2$O | 255 | 1.03 | 71 | | 7.59 |
| 17 | 1:1.5 | Mg$_3$Al$_2$(OH)$_{10}$(CO$_3$)$_2$.4 H$_2$O | 268 | 1.15 | 101 | | 7.59 |
| 18 | 1:1.5 | Mg$_3$Al$_2$(OH)$_8$(C$_6$H$_6$O$_7$)$_2$.4 H$_2$O | 375 | 0.06 | 37 | | am.* |
| 19 | 1:3 | Zn$_6$Al$_2$(OH)$_{18}$.4 H$_2$O | 180 | 0.44 | 100 | | am.* |

Legend:
*C = compound
a = activated for 3 hours at 550° C.
Surf. = surface area
b = measured on the hydrate
PV = pore volume
PR = pore radius
CS = crystallite size TABLE I-continued

| C.* | Al/M²⁺ | Formula | Surf.*ᵃ [m²g] | PV*ᵃ [ml/g] | PR*ᵃ [Å] | CS*ᵇ [Å] | dV*ᵇ [Å] |
|---|---|---|---|---|---|---|---| dV = d-value
am. = amorphous

Metal hydroxides are important precursors for the production of metal oxides. The metal oxides produced according to the invention are used as high-purity raw materials for the production of refractories, ceramics, and catalyst supports. The metal hydroxides can be used as highpurity, inorganic ion-exchange materials and mole sieves, as anticarious additives for tooth pastes, or as antacids, and as additives for plastics, e.g. flame retardants and yellowing inhibitors for PVC.

The stratiform, anionic clay minerals are produced in high purities. This is achieved by the process of the invention which comprises reacting the metals with alcohols yielding alcoholates, followed by purification of the alcoholates, e.g. by filtration. Table II gives a survey of the analytical data of several compounds produced according to the invention, of the starting metals used and of reference products obtained by the conversion of metal salts. Reference product A (RP-A) was produced from metal salts, namely reagent-grade nitrate salts, as reported in literature. Reference product B (RP-B) was produced by conversion of metal hydroxides.

hydroxide/magnesium hydroxide solution. Aluminium hydroxide and magnesium hydroxide are present in unchanged quantities; no clay minerals were formed.

Mixed metal oxides can be produced by calcination of the compounds produced according to this invention. For calcination, the compounds of the invention were placed into a muffle furnace heated to 550° C.–1,500° C. at which temperatures they were kept for 3 to 24 hours. The mixed metal oxides thus produced had the same high purities as the mixed metal hydroxides of the invention.

The surface areas of calcined compounds obtained at different calcination temperatures are presented in Table III. In order to demonstrate the great surface stability of the compounds produced according to the invention in comparison with a product obtained by mixing metal hydroxides, reference product B (RP-B) was calcined under the same conditions. The metals ratio in reference product B is the same as in $Mg_6Al_2(OH)_{18} \cdot 4H_2O$ produced according to the invention.

TABLE II

Analytical Results of Trace Elements Determination by ICP

| Substance | Si [ppm] | Fe [ppm] | Mn [ppm] | Ti [ppm] | Zn [ppm] | Ga [ppm] | Na [ppm] | Ca [ppm] | Cu [ppm] | Pb [ppm] |
|---|---|---|---|---|---|---|---|---|---|---|
| Mg (powder) | 64 | 204 | 129 | <1 | 13 | <5 | 86 | 11 | 10 | 75 |
| Mg (granules) | 46 | 286 | 8 | 3 | 23 | <5 | 23 | 9 | 3 | 90 |
| Al (needles) | 980 | 2,387 | 45 | 36 | 147 | 98 | 25 | 8 | 22 | 22 |
| RP-A | 303 | 84 | 3 | 2 | 4 | 6 | 890 | 114 | <2 | 46 |
| RP-B | 620 | 300 | 11 | <1 | 11 | <5 | 40 | 1,650 | <2 | 40 |
| 6 | 50 | 68 | 8 | <1 | 15 | <5 | 5 | 8 | <2 | <10 |
| 3 | 62 | 70 | 15 | <1 | 5 | <5 | 6 | 17 | <2 | 40 |
| 1 | 60 | 75 | 19 | <2 | 25 | <5 | 6 | 11 | <2 | 20 |
| 9 | 58 | 72 | 8 | 1 | 15 | <5 | 6 | 20 | 4 | 10 |

Magnesium powder or granules and aluminium needles (see Table II) were used for producing the compounds of the invention. The data listed in Table II confirm that the compounds produced according to the invention have the desired high purities required for numerous applications. A particular advantage is the significantly lower content of alkali—and alkaline earth metals (sodium and calcium) and of silicon and iron all of which have undesirable effects in catalysis.

The X-ray diffraction patterns depictd in FIG. 1 and FIG. 2 are typical of the compounds produced according to the invention. For comparison, FIG. 3 shows the x-ray diffraction pattern of a compound produced from an aluminium

TABLE III

Surface Areas of Calcined Compounds

| Compound/ Surface Area [m²/g] | 3h/ 550° C. | 3h/ 750° C. | 3h/ 950° C. | 3h/ 1,200° C. | 3h/ 1,500° C. |
|---|---|---|---|---|---|
| $Mg_6Al_2(OH)_{18} \cdot 4H_2O$ | 190 | 132 | 106 | 33 | 6 |
| RP-B | 138 | 73 | 43 | 32 | 1 |

Table IV shows a list of metal hydroxides produced according to the invention and the metal oxides produced therefrom by calcination.

TABLE IV

Metal Oxides from Metal Hydroxide Precursors

| Compound | Hydroxide Precursor | Calcined Product |
|---|---|---|
| 1 | $MgAl_2(OH)_8 \cdot 4 H_2O$ | $MgAl_2O_4$ |
| 2 | $Mg_2Al_2(OH)_{10} \cdot 4 H_2O$ | $Mg_2Al_2O_5$ |
| 3 | $Mg_5Al_4(OH)_{22} \cdot 4 H_2O$ | $Mg_5Al_4O_{11}$ |
| 6 | $Mg_6Al_2(OH)_{18} \cdot 4 H_2O$ | $Mg_6Al_2O_9$ |

The x-ray diffraction pattern of a spinel obtained from compound 1 in Table I is depicted in FIG. 4. For comparison, the dashed line shows the x-ray diffraction pattern recorded in the JCPDS file (entry No. 21-1152, $MgAl_2O_4$, spinel, syn). Thus, it has been proved that a pure-phase spinel, $MgAl_2O_4$, can be produced by calcining compound 1 according to this invention.

EXAMPLES

General

For the analysis of the compounds produced according to the invention, the metal ratios were determined by inductive plasma spectroscopy. The contaminants were determined by the same method. The crystalline phases, crystallite sizes, and d-spacings on the d(001) and d(003) reflexes were determined by powder diffractometry. The presence of interstitial ions ($OH^-$, $HCO_3^{31}$, $NO_3^{31}$, etc.) was proved by thermogravimetric analysis. The quantity of the water of crystallisation was determined by the same method. The quantities found were stated as percent by weight. The surface areas and pore radii were determined by the BET method (three-point method), while the pore volumes were determined by mercury porosimetry. The water content and the quantity of ions located between the layers were determined by thermogravimetric analysis. The compounds of the invention were calcined in a muffle furnace at temperatures of between 550° C. and 1,500° C.

Example 1

Compound 1 in Table I

Into a 1,000-ml three-neck flask there was placed 15.5 g of aluminium needles and 6.5 g of magnesium granules, followed by addition of 239.6 g of hexanol. The mixture was heated. Reaction of the metals with hexanol started at approx. 160° C. which was indicated by formation of hydrogen and a temperature increase to approx. 230° C. Then 534.5 g of hexanol was added to the flask through a dropping funnel. The addition took 60 minutes. The reaction mixture was filtered at 90° C. The filtrate was divided into three aliquot portions which were hydrolysed in a receiver holding 723.5 g of deionised water containing 0.2 wt. % ammonia. A white precipitate formed immediately. The supernatant alcohol was decanted (optionally, small amounts of alcohol dissolved in the aqueous phase can be stripped by steam distillation). The resultant slurry was spray dried. The yield was 98% of theoretical. ICP analysis showed an alumina/magnesium oxide ratio of 73.2%:26.8% (73%:27%, calculated). Results found by thermogravimetric analysis: residue 50.3% of $MgAl_2O_4$ (49.7% of theoretical), -$4H_2O$ (water of crystallisation) 24.9% (25.2% of theoretical), -$4H_2O$ 25.4% (25.2% of theoretical).

Example 2

Compound 6 in Table I

Into a 1,000-ml three-neck flask there was placed 7.9 g of aluminium needles and 21.1 g of magnesium granules, followed by addition of 122.0 g of hexanol. The mixture was heated. Reaction of the metals with hexanol started at approx. 160° C. which was indicated by formation of hydrogen and a temperature increase to approx. 230° C. Then 574.0 g of hexanol was added to the flask through a dropping funnel. The addition took 60 minutes. The reaction mixture was filtered at 90° C. The filtrate was divided into three aliquot portions which were hydrolysed in a receiver holding 943.0 g of deionised water containing 0.2 wt. % ammonia. A white precipitate formed immediately. The supernatant alcohol was decanted (optionally, small amounts of alcohol dissolved in the aqueous phase can be stripped by steam distillation). The resultant slurry was spray dried. The yield was 98% of theoretical. ICP analysis showed an alumina/magnesium oxide ratio of 32.2%:67.8% (30%:70%, calculated). Results found by thermogravimetric analysis: residue 60.2% of $Mg_6Al_2O_9$ (59.5% of theoretical), -$4H_2O$ (water of crystallisation) 13.2% (12.5% of theoretical), -$9H_2O$ 27.0% (28.0% of theoretical).

Example 3

Compound 9 in Table I

Into a 1,000-ml three-neck flask there was placed 7.9 g of aluminium needles and 21.1 g of magnesium granules, followed by addition of 117.0 g of hexanol. The mixture was heated. Reaction of the metals with hexanol started at approx. 160° C. which was indicated by formation of hydrogen and a temperature increase to approx. 230° C. Then 574.0 g of hexanol was added to the flask through a dropping funnel. The addition took 60 minutes. The reaction mixture was filtered at 90° C. The filtrate was divided into three aliquot portions which were hydrolysed in a receiver holding 876.0 g of deionised water containing 32.2 g of ammonium nitrate. A white precipitate formed immediately. The supernatant alcohol was decanted (optionally, small amounts of alcohol dissolved in the aqueous phase can be stripped by steam distillation). The resultant slurry was spray dried. The yield was 98% of theoretical. ICP analysis showed an alumina/magnesium oxide ratio of 30.8%:69.2% (30%:70%, calculated). Results found by thermogravimetric analysis: residue 52.5% of $Mg_6Al_2O_9$ (51.5% of theoretical), -$4H_2O$ (water of crystallisation) 10.6% (10.8% of theoretical), -$5H_2O$ 12.5% (13.5% of theoretical), -$2H_2O$ -$2HNO_3$ 24.9% (24.3% of theoretical).

Example 4

Compound 11 in Table I

Into a 1,000-ml three-neck flask there was placed 7.9 g of aluminium needles and 21.1 g of magnesium granules, followed by addition of 118.0 g of hexanol. The mixture was heated. Reaction of the metals with hexanol started at approx. 160° C. which was indicated by formation of hydrogen and a temperature increase to approx. 230° C. Then 574.0 g of hexanol was added to the flask through a dropping funnel. The addition took 60 minutes. The reaction mixture was filtered at 90° C. The filtrate was divided into three aliquot portions which were hydrolysed in a receiver holding 872.0 g of deionised water containing 27.8 g of ammonium carbonate. A white precipitate formed immediately. The supernatant alcohol was decanted (optionally, small amounts of alcohol dissolved in the aqueous phase can be stripped by steam distillation). The resultant slurry was spray dried. The yield was 98% of theoretical. ICP analysis showed an alumina/magnesium oxide ratio of 31.8%:68.2% (30%:70%, calculated). Results found by thermogravimetric analysis: residue 56.3% of $Mg_6Al_2O_9$ (56.9% of theoretical), -$4H_2O$ (water of crystallisation) -$1H_2O$ 15.2% (14.9% of theoretical), -$6H_2O$—$H_2CO_3$ 28.7% (28.2% of theoretical).

Example 5
Compound 12 in Table I

Into a 1,000-ml three-neck flask there was placed 8.0 g of aluminium needles and 21.1 g of magnesium granules, followed by addition of 118.0 g of hexanol. The mixture was heated. Reaction of the metals with hexanol started at approx. 160° C. which was indicated by formation of hydrogen and a temperature increase to approx. 230° C. Then 574.0 g of hexanol was added to the flask through a dropping funnel. The addition took 60 minutes. The reaction mixture was filtered at 90° C. The filtrate was divided into three aliquot portions which were hydrolysed in a receiver holding 542.0 g of deionised water containing 358.0 g of ammonium molybdate, $(NH_4)_6Mo_7O_{24}$. A white precipitate formed immediately. The supernatant alcohol was decanted (optionally, small amounts of alcohol dissolved in the aqueous phase can be stripped by steam distillation). The resultant slurry was spray dried. The yield was 98% of theoretical. ICP analysis showed an alumina/magnesium oxide ratio of 30.9%:69.1% (30%: 70%, calculated) and a $Mo_7O_{24}$ content of 42.0% (41.5% of theoretical). Results found by thermogravimetric analysis: residue 82.1% of $Mg_{18}Al_6O_{27}$ +$MO_7O_{24}$ (79.0% of theoretical), -12$H_2O$ (water of crystallisation) -24$H_2O$ 21.0% (23.7% of theoretical).

Example 6
Compound 17 in Table I

Into a 1,000-ml three-neck flask there was placed 11.3 g of aluminium needles and 15.1 g of magnesium granules, followed by addition of 176.0 g of hexanol. The mixture was heated. Reaction of the metals with hexanol started at approx. 160° C. which was indicated by formation of hydrogen and a temperature increase to approx. 230° C. Then 456.0 g of hexanol was added to the flask through a dropping funnel. The addition took 60 minutes. The reaction mixture was filtered at 90° C. The filtrate was divided into three aliquot portions which were hydrolysed in a receiver holding 782.0 g of deionised water containing 39.8 g of ammonium carbonate. A white precipitate formed immediately. The supernatant alcohol was decanted (optionally, small amounts of alcohol dissolved in the aqueous phase can be stripped by steam distillation). The resultant slurry was spray dried. The yield was 98% of theoretical. ICP analysis showed an alumina/magnesium oxide ratio of 49.0%:51.0% (46%:54%, calculated). Results found by thermogravimetric analysis: residue 53.0% of $Mg_3Al_2O_6$ (52.0% of theoretical), -4$H_2O$ (water of crystallisation) -$H_2O$ 19.9% (21.0% of theoretical), -3$H_2O$—$H_2CO_3$ 25.1% (27.1% of theoretical).

Example 7
Compound 18 in Table I

Into a 1,000-ml three-neck flask there was placed 11.3 g of aluminium needles and 15.1 g of magnesium granules, followed by addition of 176.0 g of hexanol. The mixture was heated. Reaction of the metals with hexanol started at approx. 160° C. which was indicated by formation of hydrogen and a temperature increase to approx. 230° C. Then 456.0 g of hexanol was added to the flask through a dropping funnel. The addition took 60 minutes. The reaction mixture was filtered at 90° C. The filtrate was divided into three aliquot portions which were hydrolysed in a receiver holding 729.0 g of deionised water containing 92.7 g of ammonium citrate, $(NH_4)_2C_6H_6O_7$. A white precipitate formed immediately. The supernatant alcohol was decanted (optionally, small amounts of alcohol dissolved in the aqueous phase can be stripped by steam distillation). The resultant slurry was spray dried. The yield was 98% of theoretical. ICP analysis showed an alumina/magnesium oxide ratio of 49.7%:50.3% (46%: 54%, calculated). Results found by thermogravimetric analysis: residue 42.9% of $Mg_3Al_2O_6$ (39.9% of theoretical), -4$H_2O$ (water of crystallisation) 13.4% (12.9% of theoretical), -4$H_2O$—$C_6H_8O_7$ 42.9% (38.7% of theoretical).

Example 8
Compound 6 in Table I, but Separate Preparation of the Metal Alcoholates Into a 500-ml three-neck flask there was placed 7.9 g of aluminium needles, followed by addition of 50.0 g of hexanol. The mixture was heated. Reaction of the metal with hexanol started at approx. 160° C. which was indicated by formation of hydrogen and a temperature increase to approx. 230° C. Then 220.0 g of hexanol was added to the flask through a dropping funnel. The addition took 60 minutes. The reaction mixture was filtered at 90° C. Into a 500-ml three-neck flask there was placed 21.1 g of magnesium granules, followed by addition of 120.0 g of hexanol. The mixture was heated. Reaction of the metal with hexanol started at approx. 150° C. which was indicated by formation of hydrogen and a temperature increase to approx. 200° C. Then 307.0 g of hexanol was added to the flask through a dropping funnel. The addition took 60 minutes. The reaction mixture was filtered at 90° C. The two alcoholates were combined. The quantity obtained was divided into three aliquot portions which were hydrolysed in a receiver holding 943.0 g of deionised water containing 0.2 wt. % ammonia. A white precipitate formed immediately. The supernatant alcohol was decanted (optionally, small amounts of alcohol dissolved in the aqueous phase can be stripped by steam distillation). The resultant slurry was spray dried. The yield was 98% of theoretical. ICP analysis showed an alumina/magnesium oxide ratio of 32.1%:67.9% (30%:70%, calculated). Results found by thermogravimetric analysis: residue 60.1% of $Mg_6Al_2O_9$ (59.5% of theoretical), -4$H_2O$ (water of crystallisation) 13.3% (12.5% of theoretical), -9$H_2O$ 26.9% (28.0% of theoretical).

Example 9
Compound 6 in Table I, but use of Mixed Alcohols

Into a 1,000-ml three-neck flask there was placed 7.9 g of aluminium needles and 21.1 g of magnesium granules, followed by addition of 120.0 g of a mixture of butanol, hexanol, and octanol (1:7:2). The mixture was heated. Reaction of the metals with the alcohol mixture started at approx. 150° C. which was indicated by formation of hydrogen and a temperature increase to approx. 210° C. Then 552.0 g of the alcohol mixture was added to the flask through a dropping funnel. The addition took 60 minutes. The reaction mixture was filtered at 90° C. The filtrate was divided into three aliquot portions which were hydrolysed in a receiver holding 900.0 g of deionised water containing 0.2 wt.% ammonia. A white precipitate formed immediately. The supernatant alcohol was decanted. Butanol and small amounts of hexanol and octanol dissolved in the aqueous phase were stripped by steam distillation. The resultant slurry was spray dried. The yield was 97% of theoretical. ICP analysis showed an alumina/magnesium oxide ratio of 32.2%:67.8% (30%: 70%, calculated). Results found by thermogravimetric analysis: residue 60.4% of $Mg_6Al_2O_9$ (59.5% of theoretical), -4$H_2O$ (water of crystallisation) 13.0% (12.5% of theoretical), -9$H_2O$ 27.1% (28.0% of theoretical).

Example 10

Compound 19 in Table I Conversion of a Metal Alcoholate and a Metal Plus Alcohol Into a 1,000-ml three-neck flask there was placed 7.9 g of aluminium needles, followed by addition of 50.0 g of hexanol. The mixture was heated. Reaction of the metal with the alcohol started at approx. 160° C. which was indicated by formation of hydrogen and a temperature increase to approx. 230° C. Then 220.0 g of hexanol was added to the flask through a dropping funnel. The addition took 60 minutes. Then 115.3 g of zinc diethanolate was added. The mixture was allowed to cool to 90° C. prior to filtration. The filtrate was divided into three aliquot portions which were hydrolysed in a receiver holding 510.0 g of deionised water containing 0.2 wt. % ammonia. A white precipitate formed immediately. The supernatant alcohol was decanted (optionally, small amounts of the alcohol dissolved in the aqueous phase can be stripped by steam distillation). The resultant slurry was spray dried. The yield was 96% of theoretical. ICP analysis showed an alumina/zinc oxide ratio of 16.8%:83.2% (17%:83%, calculated). Results found by thermogravimetric analysis: residue 72.2% of $Zn_6Al_2O_9$ (71.6% of theoretical), $-4H_2O$ (water of crystallisation) 9.1% (8.7% of theoretical), $-9H_2O$ 19.5% (19.7% of theoretical).

What is claimed is:

1. A process for producing high purity hydrotalcites which are stratiform, anionic mixed metal hydroxides of the general formula $$M_{2x}^{2+} M_2^{3+}(OH)_{4x+4} \cdot A_{2/n}^{n-} \cdot zH_2O$$

wherein $M_{2x}^{2+}$, $M_2^{3+}$ are divalent and trivalent metal(s) respectively, x ranges from 0.5 to 10 in intervals of 0.5, A is an interstitial anion selected from the group consisting of a hydroxide anion and an organic anion, n is the charge of said interstitial anion, and z is an integer of 1 to 6, comprising (A) mixing at least one divalent metal alcoholate with at least one trivalent metal alcoholate, both metal alcoholates being metal alcoholates of mono-, di-, or trihydric C1 to C40 alcoholates, where said mono-, di- and trihydric metal alcoholates being mixed in a molar ratio corresponding to the stoichiometry of the formula referred to hereinabove, and (B) hydrolyzing the resultant alcoholate mixture with water, the water for hydrolysis being used in stoichiometric excess, referring to the reactive valences of the metals used and where the source of the interstitial anions for A is from the water-soluble anions contained in the water for hydrolysis.

2. A process for producing metal oxides by calcinating the hydrotalcites produced according to claim 1.

3. A process according to claim 1 wherein the metal alcoholates are first produced by reacting metals having the oxidation numbers +II or +III with the alcohols according to claim 1, the production of said metal alcoholates being accomplished by a process element selected from the group consisting of (A) placing the metals jointly into the reaction vessel and then adding the alcohol, (B) producing the metal alcoholates separately, the alcoholates having same or different alcoholate residues, and (C) consecutively, by placing one metal into the reaction vessel, adding the alcohol, followed by addition of the second metal.

4. A process according to claim 1 wherein the divalent metals used are selected from the group consisting of Mg, Zn, Cu, Ni, Co, Mn, Ca and Fe and the trivalent metals used are selected from the group consisting of Al, Fe, Co, Mn, La, Ce and Cr.

5. A process according to claim 1 wherein, prior to or during the hydrolysis, as a third or additional metal component, water-soluble, di- and/or trivalent metals as metal salts are added, the metal salts being used in molar quantities smaller than the metal alcoholates, and the total molar ratio of the divalent: trivalent metals being as defined in claim 1.

6. A process according to claim 1 wherein for the hydrolysis, water is used which contains water-soluble anions selected from the group consisting of:

a. hydroxide anions; and b. organic anions selected from the group consisting of alcoholates alkyl ether sulfates aryl ether sulfates and glycol ether sulfates.

7. A process according to claim 1 wherein prior to hydrolysis the metal alcoholate mixture is filtered.

8. The process of claim 3 where in process element (C) further amounts of alcohol are added after the addition of the second metal.

9. The process of claim 6 where the organic anions are selected from the group consisting of alcoholates, alkyl ether sulfates, aryl ether sulfates, and glycol ether sulfates.

10. The process of claim 6 where the counterion is ammonium and the anion is hydroxide ion.

11. A process for producing high purity hydrotalcites which are stratiform, anionic mixed metal hydroxides of the general formula $$M_{2x}^{2+} M_2^{3+}(OH)_{4x+4} \cdot A_{2/n}^{n-} \cdot zH_2O$$

wherein $M_{2x}^{2+}$, $M_2^{3+}$ are divalent and trivalent metal(s) respectively, x ranges from 0.5 to 10 in intervals of 0.5, A is an interstitial anion selected from the group consisting of a hydroxide anion and an organic anion, n is the charge of said interstitial anion, and z is an integer of 1 to 6, comprising (A) mixing at least one divalent metal alcoholate where the metal is selected from the group consisting of Mg, Zn, Cu, Ni, Co, Mn, Ca and Fe, with at least one trivalent metal alcoholate where the metal is selected from the group consisting of Al, Fe, Co, Mn, La, Ce and Cr, and both metal alcoholates being metal alcoholates of mono-, di-, or trihydric C1 to C40 alcoholates, where said mono-, di- and trihydric metal alcoholates being mixed in a molar ratio corresponding to the stoichiometry of the formula referred to hereinabove, and (B) hydrolyzing the resultant alcoholate mixture with water, the water for hydrolysis being used in stoichiometric excess, referring to the reactive valences of the metals used, and where the hydrolysis water used contains water-soluble, organic or inorganic anions and where the source of the interstitial anions for A is from the water-soluble anions contained in the water for hydrolysis.

12. A process for producing metal oxides by calcinating the hydrotalcites produced according to claim 11.

13. The process according to claim 11 wherein the metal alcoholates are first produced by reacting metals having the oxidation numbers +II or +III with the alcohols according to claim 11, the production of said metal alcoholates being accomplished by a process element selected from the group consisting of (A) placing the metals jointly into the reaction vessel and then adding the alcohol, (B) producing the metal alcoholates separately, the alcoholates having same or different alcoholate residues, and (C) consecutively, by placing one metal into the reaction vessel, adding the alcohol, followed by addition of the second metal.

14. The process according to claim 11 wherein, prior to or during the hydrolysis, as a third or additional metal component, water-soluble, di- and/or trivalent metals as metal salts are added, the metal salts being used in molar quantities smaller than the metal alcoholates, and the total molar ratio of the divalent: trivalent metals being as defined in claim 1.

15. The process according to claim 11 wherein for the hydrolysis water contains water-soluble anions selected from the group consisting of:
   a. hydroxide anions; and
   b. organic anions selected from the group consisting of alcoholates, alkyl ether sulfates, aryl ether sulfates, and glycol ether sulfates.

16. A process for producing high purity hydrotalcites which are stratiform, anionic mixed metal hydroxides of the general formula $$M_{2x}^{2+}M_2^{3+}(OH)_{4x+4} \cdot A_{2/n}^{n-} \cdot zH_2O$$

wherein $M_{2x}^{2+}$, $M_2^{3+}$ are divalent and trivalent metal(s) respectively, x ranges from 0.5 to 10 in intervals of 0.5, A is an interstitial anion selected from the group consisting of a hydroxide anion and an organic anion, n is the charge of said interstitial anion, and z is an integer of 1 to 6, comprising (A) mixing at least one divalent metal alcoholate with at least one trivalent metal alcoholate, both metal alcoholates being metal alcoholates of and mono-, di-, or trihydric C1 to C40 alcoholates, where said mono-, di- and trihydric metal alcoholates being mixed in a molar ratio corresponding to the stoichiometry of the formula referred to hereinabove, and where the production of said metal alcoholates being accomplished by a process element selected from the group consisting of
   (i) placing the metals jointly into the reaction vessel and then adding the alcohol,
   (ii) producing the metal alcoholates separately, the alcoholates having same or different alcoholate residues, and
   (iii) consecutively, by placing one metal into the reaction vessel, adding the alcohol, followed by addition of the second metal (B) filtering the metal alcoholate mixture,
(C) hydrolyzing the resultant alcoholate mixture with water, the water for hydrolysis being used in stoichiometric excess, referring to the reactive valences of the metals used and where the source of the interstitial anions for A is from the water-soluble anions contained in the water for hydrolysis.

17. The process according to claim 16 wherein the divalent metals used are selected from the group consisting of Mg, Zn, Cu, Ni, Co, Mn, Ca and Fe and the trivalent metals used are selected from the group consisting of Al, Fe, Co, Mn, La, Ce and Cr.

18. The process according to claim 16 wherein for the hydrolysis water contains water-soluble anions selected from the group consisting of:
   a. hydroxide anions; and
   b. organic anions selected from the group consisting of alcoholates, alkyl ether sulfates, aryl ether sulfates, and glycol ether sulfates.

* * * * *